United States Patent [19]

Zipplies et al.

[11] Patent Number: 5,064,828

[45] Date of Patent: Nov. 12, 1991

[54] FUNGICIDAL MIXTURE

[75] Inventors: Matthias Zipplies, Hirschberg; Hubert Sauter, Mannheim; Randall E. Gold, Wachenheim; Alan Akers, Heidelberg; Eberhard Ammermann, Ludwigshafen; Gisela Lorenz, Neustadt, all of Fed. Rep. of Germany

[73] Assignee: BASF Aktiengesellschaft, Ludwigshafen, Fed. Rep. of Germany

[21] Appl. No.: 470,229

[22] Filed: Jan. 25, 1990

[30] Foreign Application Priority Data

Jan. 28, 1989 [DE] Fed. Rep. of Germany ....... 3902509

[51] Int. Cl.$^5$ .................... A01N 33/02; A01N 43/84
[52] U.S. Cl. ................................. 514/239.5; 514/654
[58] Field of Search .............................. 514/239.5, 654

[56] References Cited

U.S. PATENT DOCUMENTS 3,468,885 9/1969 Sanne et al. ...................... 260/247.2
4,282,251 8/1981 Berney ............................. 260/501.1

FOREIGN PATENT DOCUMENTS 1591267 6/1981 United Kingdom .

Primary Examiner—Allen J. Robinson
Attorney, Agent, or Firm—Oblon, Spivak, McClelland, Maier & Neustadt

[57] ABSTRACT

A fungicidal mixture of
a) a compound of the formula I

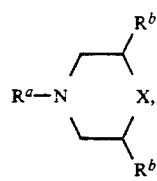

where
$R^a$ = tridecyl or 3-(p-tert-butyl-(phenyl)-2-methylpropyl, $R^b$ = H, CH$_3$ and
X = O, CH$_2$ and b) a compound of the formula II

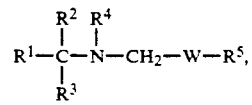

where
$R^1$ is substituted or unsubstituted phenyl, naphthyl, tetrahydronaphthyl, benzothiophenyl, benzofuranyl, anthracenyl, acenaphthenyl, hexahydroindacenyl, tetrahydrophenanthrenyl, stilbenyl or benzodioxolanyl,
$R^2$ is hydrogen or methyl,
$R^3$ is hydrogen,
$R^4$ is alkyl, cyclopropyl, haloalkyl or alkenyl,
W is alkenylene, fluoroalkenylene or a single bond,
$R^5$ is substituted or unsubstituted phenyl, or is naphthyl, substituted or unsubstituted alkenyl, or alkynyl, where the radical

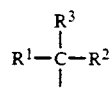

may denote the acenaphthenyl radical

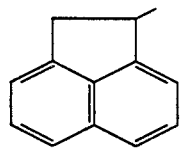

and the radical

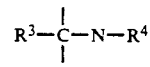

may also be part of a heterocyclic ring.

3 Claims, No Drawings

FUNGICIDAL MIXTURE

The present invention relates to fungicidal mixtures for crop protection, containing a mixture of at least two active ingredients.

N-Tridecyl-2,6-dimethylmorpholine (tridemorph) is a well-known fungicide (U.S. Pat. No. 3,468,885). The use of N-[3-(p-tert-butylphenyl)-2-methylpropyl]-cis-2,6-dimethylmorpholine (fenpropimorph) and N-[3-(p-tert-butylphenyl)-2-methylpropyl]-piperidine (fenpropidin) as fungicides has also been disclosed (DE-2 656 747.5).

It is further known to use amino derivatives, e.g., N-methyl-N-allylphenylnaphthyl-1-methylamine, for combating fungi in medicine (DE-2 716 943).

We have now found that a fungicidal mixture of
a) a compound of the formula I

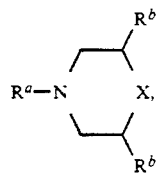

where
$R^a$ = tridecyl ($C_{13}H_{27}$ isomer mixture), 3-(p-tert-butyl-(phenyl)-2-methylpropyl,
$R^b$ = H, $CH_3$ (cis or trans) and
X = O, $CH_2$
and
b) a compound of the formula II

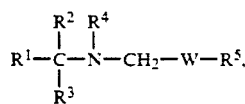

where
$R^1$ is unsubstituted phenyl or phenyl which is mono- to trisubstituted by $C_1$-$C_4$-alkyl, $C_2$-$C_4$-alkenyl, $C_2$-$C_6$-alkoxyalkyl, halogen, hydroxyl, $C_1$-$C_4$-alkoxy or cyano, or is naphthyl, tetrahydronaphthyl, benzothiophenyl, benzofuranyl, anthracenyl, acenaphthenyl, hexahydroindacenyl, tetrahydrophenanthrenyl, stilbenyl or benzodioxolanyl,
$R^2$ is hydrogen or methyl
$R^3$ is hydrogen
$R^4$ is $C_1$-$C_3$-alkyl, cyclopropyl, $C_2$-haloalkyl or $C_3$-alkenyl W is $C_2$-alkenylene, $C_2$-fluoroalkenylene or a single bond,
$R^5$ is unsubstituted phenyl or phenyl which is mono- to trisubstituted by halogen, $C_1$-$C_4$-alkyl, hydroxyl or $C_1$-$C_5$-alkoxy, or is naphthyl, $C_3$-$C_8$-alkenyl which is unsubstituted or mono- to trisubstituted by hydroxyl, $C_1$-$C_5$-alkoxy, $C_3$-$C_6$-cycloalkyl, aryl, thiophenyl, cyano or halogen, or is $C_3$-$C_8$-alkynyl, where the radical

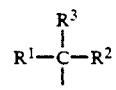

may denote the acenaphthenyl radical

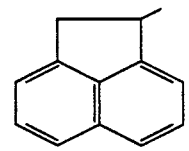

and the radical

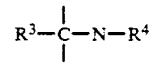

may also be part of a saturated 5- or 6-membered heterocyclic ring with, if desired, an additional oxygen or sulfur atom and 3 to 5 carbon atoms. The ratio of a) to b) is selected so that a synergistic action occurs, for example in a weight ratio of a) to b) of from 1:100 to 10:1, especially from 1:20 to 5:1, and preferably 1:10 to 2:1. A ratio of from 1:10 to 2:1 is preferred, and particularly preferably from 1:5 to 1:1.
$R^1$ is for example α-naphthyl, methylnaphthyl, methoxynaphthyl or dichlorophenyl
$R^4$ is for example methyl or ethyl
W is for example an ethenylene radical or a single bond
$R^5$ is for example 3,3-dimethylbut-1-ynyl, phenyl, naphthyl, tert-butylphenyl, methoxyphenyl or chlorophenyl.

A mixture of
a) fenpropimorph with
b) compound no. 1, especially in a weight ratio of a:b such as 1:1, is preferred.

Examples of suitable active ingredients of group b) are given in the following table.

TABLE 1

Compounds b $$R^1-\underset{\underset{R^3}{|}}{\overset{\overset{R^2}{|}}{C}}-\underset{\underset{}{|}}{\overset{\overset{R^4}{|}}{N}}-CH_2-W-R^5$$

II

| No. | $R^2$ | $R^3$ | $R^4$ | W | $R^5$ | Known from |
|-----|-------|-------|-------|---|-------|------------|
| 1 | α-naphthyl | H | H | $CH_3$ | 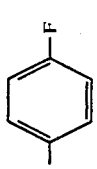 trans-ethenylene | 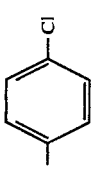 | 1,2 |
| 2 | α-naphthyl | H | H | $CH_3$ | trans-ethenylene | 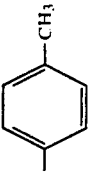 | 3 |
| 3 | α-naphthyl | H | H | $CH_3$ | trans-ethenylene | 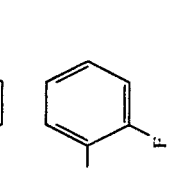 | 1 |
| 4 | α-naphthyl | H | H | $CH_3$ | trans-ethenylene |  | 1 |
| 5 | α-naphthyl | H | H | $CH_3$ | trans-ethenylene |  | 1 |
| 6 | α-naphthyl | H | H | $CH_3$ | trans-ethenylene |  | 1 |
| 7 | α-naphthyl | H | H | $CH_3$ | trans-ethenylene |  | 1 |

TABLE 1-continued
Compounds b
$$R^1-\underset{R^3}{\underset{|}{C}}-\underset{|}{\overset{R^2}{N}}-CH_2-W-R^5 \quad II$$
| No. | R¹ | R² | R³ | R⁴ | W | R⁵ | Known from |
|---|---|---|---|---|---|---|---|
| 8 | α-naphthyl | H | H | CH₃ | trans-ethenylene | 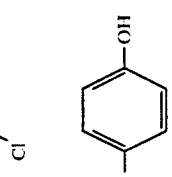 | 1 |
| 9 | α-naphthyl | H | H | CH₃ | trans-ethenylene | 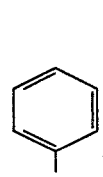 | 2 |
| 10 | α-naphthyl | H | H | isopropyl | trans-ethenylene | 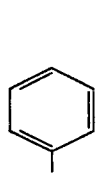 | 2 |
| 11 | α-naphthyl | H | H | allyl | trans-ethenylene | 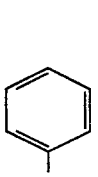 | 2 |
| 12 | 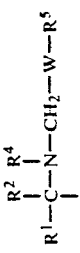 | H | H | CH₃ | trans-ethenylene | 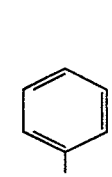 | 2 |
| 13 |  | H | H | CH₃ | trans-ethenylene | | 2 |

TABLE 1-continued

Compounds b $$R^1-\underset{\underset{R^3}{|}}{\overset{\overset{R^2}{|}}{C}}-\overset{\overset{R^4}{|}}{N}-CH_2-W-R^5 \quad II$$

| No. | R¹ | R² | R³ | R⁴ | W | R⁵ | Known from |
|---|---|---|---|---|---|---|---|
| 14 | 4-chloro-1-naphthyl | H | H | CH₃ | trans-ethenylene | phenyl | 2 |
| 15 | 4-methyl-1-naphthyl | H | H | CH₃ | trans-ethenylene | phenyl | 2 |
| 16 | 2-methoxy-1-naphthyl | H | H | CH₃ | trans-ethenylene | phenyl | 2 |
| 17 | 4-methoxy-1-naphthyl | H | H | CH₃ | trans-ethenylene | phenyl | 2 |
| 18 | 1-naphthyl | CH₃ | H | CH₃ | trans-ethenylene | phenyl | 2 |
| 19 | 1-naphthyl | H | H | CH₃ | trans-ethenylene | —C≡C—(CH₂)₃—CH₃ | 3 |

TABLE 1-continued

Compounds b $$R^1-\overset{R^2}{\underset{R_3}{\overset{|}{C}}}-\overset{R^4}{\underset{}{\overset{|}{N}}}-CH_2-W-R^5 \quad II$$

| No. | R¹ | R² | R³ | R⁴ | W | R⁵ | Known from |
|---|---|---|---|---|---|---|---|
| 21 | 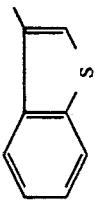 | H | H | CH₃ | trans-ethenylene | $-C\equiv C-\underset{CH_3}{\overset{CH_3}{\overset{|}{\underset{|}{C}}}}-OH$ | 3 |
| 22 | 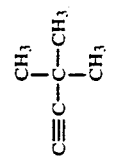 | H | H | CH₃ | trans-ethenylene | $-C\equiv C-(CH_2)_3-CH_3$ | 3 |
| 23 | 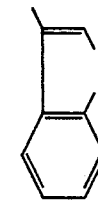 | H | H | CH₃ | trans-ethenylene | $-C\equiv C-(CH_2)_3-CH_3$ | 3 |
| 24 | 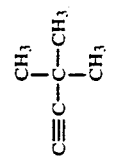 | H | H | CH₃ | trans-ethenylene | $-C\equiv C-(CH_2)_3-CH_3$ | 3 |
| 25 | 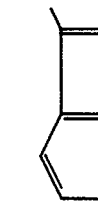 | H | H | CH₃ | trans-ethenylene | $-C\equiv C-\underset{CH_3}{\overset{CH_3}{\overset{|}{\underset{|}{C}}}}-CH_3$ | 3 |
| 26 | 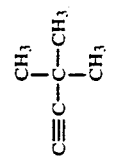 |  |  | CH₃ | trans-ethenylene | $-C\equiv C-\underset{CH_3}{\overset{CH_3}{\overset{|}{\underset{|}{C}}}}-CH_3$ | 3 |

TABLE 1-continued
Compounds b
$$R^1-\underset{\underset{R^3}{|}}{\overset{\overset{R^2}{|}}{C}}-\underset{\underset{}{|}}{\overset{\overset{R^4}{|}}{N}}-CH_2-W-R^5 \quad II$$
| No. | R¹ | R² | R³ | R⁴ | W | R⁵ | Known from |
|---|---|---|---|---|---|---|---|
| 27 | 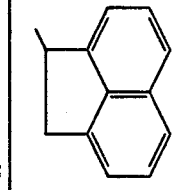 | H | H | CH₃ | trans-ethenylene |  | 3 |
| 28 | 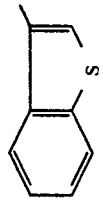 | H | H | CH₃ | trans-ethenylene |  | 3 |
| 29 | 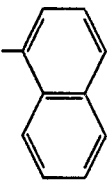 | H | H | CH₃ | trans-ethenylene | —C≡C—(CH₂)₃—CH₃ | 3 |
| 30 |  | H | H | CH₃ | trans-ethenylene | 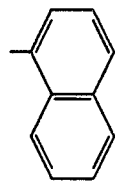 | 3 |
| 31 |  | H | H | CH₃ | trans-ethenylene | 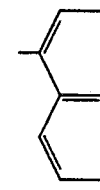 | 3 |
| 32 |  | H | H | CH₃ | trans-ethenylene | —C≡CH | 3 |

TABLE 1-continued

Compounds b $$R^1-\underset{\underset{R^3}{|}}{\overset{\overset{R^2}{|}}{C}}-N-CH_2-W-R^5 \quad II$$

| No. | R¹ | R² | R³ | R⁴ | W | R⁵ | Known from |
|---|---|---|---|---|---|---|---|
| 33 | naphthyl | H | H | R₃R₄N = piperidinyl | trans-ethenylene | —C≡CH | 3 |
| 34 | naphthyl | H | H | CH₃ | trans-ethenylene | —C≡C—C₆H₅ | 3 |
| 35 | naphthyl | H | H | CH₃ | trans-ethenylene | —C≡C—CH(CH₃)—CH₂—CH₃ | 3 |
| 36 | naphthyl | H | H | CH₃ | trans-ethenylene | —C≡C—CH₂—CH(CH₃)—CH₃ | 3 |
| 37 | naphthyl | H | H | CH₃ | trans-ethenylene | —C≡C—(2-thienyl) | 3 |
| 38 | naphthyl | H | H | CH₃ | trans-ethenylene | —C≡C—C(CH₃)₂—OH | 3 |

TABLE 1-continued

Compounds b $$R^1-\underset{\underset{R^3}{|}}{\overset{\overset{R^2}{|}}{C}}-\underset{\underset{}{|}}{\overset{\overset{R^4}{|}}{N}}-CH_2-W-R^5 \quad II$$

| No. | $R^1$ | $R^2$ | $R^3$ | $R^4$ | W | $R^5$ | Known from |
|-----|-------|-------|-------|-------|---|-------|------------|
| 39 | naphthyl | H | H | CH$_3$ | trans-ethenylene | $-C\equiv C-\underset{\underset{C_2H_5}{|}}{\overset{\overset{CH_3H_5}{|}}{C}}-OH$ | 3 |
| 40 | naphthyl | H | H | CH$_3$ | trans-ethenylene | $-C\equiv C-\underset{\underset{OH}{|}}{C}-(CH_2)_3-CH_3$ | 3 |
| 41 | naphthyl | H | H | CH$_3$ | trans-ethenylene | $-C\equiv C-\underset{\underset{OH}{|}}{\overset{\overset{CH_3}{|}}{C}}-\underset{\underset{CH_3}{|}}{\overset{\overset{CH_3}{|}}{C}}-CH_3$ | 3 |
| 42 | naphthyl | H | H | CH$_3$ | trans-ethenylene | $-C\equiv C-(CH_2)_4-CH_3$ | 3 |
| 43 | naphthyl | H | H | CH$_3$ | trans-ethenylene | $-CH_2-C_6H_5$ | 3 |
| 44 | naphthyl | H | H | CH$_3$ | trans-ethenylene | $-CH_2-\underset{\underset{CH_2}{|}}{\overset{\overset{CH_3}{|}}{C}}=\underset{\underset{CH_3}{|}}{\overset{\overset{C_2H_5}{|}}{C}}$ | 3 |

TABLE 1-continued

Compounds b $$R^1-\underset{\underset{R^3}{|}}{\overset{\overset{R^2}{|}}{C}}-\overset{\overset{R^4}{|}}{N}-CH_2-W-R^5$$
II

| No. | R¹ | R² | R³ | R⁴ | W | R⁵ | Known from |
|-----|----|----|----|----|----|----|------------|
| 45 | 1-naphthyl | H | H | CH₃ | trans-ethenylene | —CH=cyclohexylidene | 3 |
| 46 | 1-naphthyl | H | H | CH₃ | trans-ethenylene | —C≡C—CH₂OH | 3 |
| 47 | 1-naphthyl | H | H | CH₃ | trans-ethenylene | —C≡C—C(CH₃)(C₂H₅)(CH₃) | 3 |
| 48 | 1-naphthyl | H | H | CH₃ | trans-ethenylene | —C≡C-cyclopentyl | 3 |
| 49 | benzothienyl | H | H | CH₃ | trans-ethenylene | —C≡C—C(CH₃)₃ | 4 |
| 50 | benzothienyl | H | H | CH₃ | trans-ethenylene | —C≡C—C(CH₃)₃ | 4 |

TABLE 1-continued

Compounds h $$R^1-\underset{\underset{R^3}{|}}{\overset{\overset{R^2}{|}}{C}}-\underset{\underset{}{|}}{\overset{\overset{R^4}{|}}{N}}-CH_2-W-R^5 \quad II$$

| No. | R¹ | R² | R³ | R⁴ | W | R⁵ | Known from |
|---|---|---|---|---|---|---|---|
| 51 | 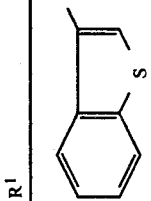 | H | H | CH₃ | trans-ethenylene | $-C{\equiv}C-\underset{\underset{CH_3}{\mid}}{\overset{\overset{CH_3}{\mid}}{C}}-CH_3$ | 4 |
| 52 | 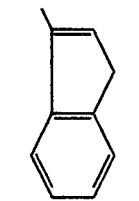 | H | H | CH₃ | trans-ethenylene | $-C{\equiv}C-\underset{\underset{CH_3}{\mid}}{\overset{\overset{CH_3}{\mid}}{C}}-C_2H_5$ | 4 |
| 53 | 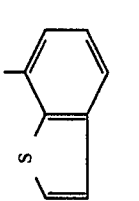 | H | H | CH₃ | trans-ethenylene | $-C{\equiv}C-\underset{\underset{CH_3}{\mid}}{\overset{\overset{CH_3}{\mid}}{C}}-CH_3$ | 4 |
| 54 | 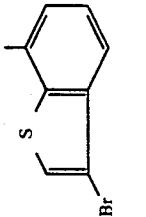 | H | H | CH₃ | trans-ethenylene | $-C{\equiv}C-\underset{\underset{CH_3}{\mid}}{\overset{\overset{CH_3}{\mid}}{C}}-CH_3$ | 4 |
| 55 | 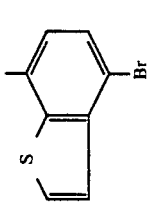 | H | H | CH₃ | trans-ethenylene | $-C{\equiv}C-\underset{\underset{CH_3}{\mid}}{\overset{\overset{CH_3}{\mid}}{C}}-CH_3$ | 4 |
| 56 | 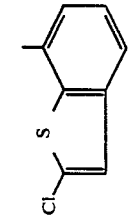 | H | H | CH₃ | trans-ethenylene | $-C{\equiv}C-\underset{\underset{CH_3}{\mid}}{\overset{\overset{CH_3}{\mid}}{C}}-CH_3$ | 4 |

TABLE 1-continued

Compounds h $$R^1-\underset{\underset{R^3}{|}}{\overset{\overset{R^2}{|}}{C}}-\underset{\underset{}{|}}{\overset{\overset{R^4}{|}}{N}}-CH_2-W-R^5$$
$$\qquad\qquad\qquad H$$

| No. | R¹ | R² | R³ | R⁴ | W | R⁵ | Known from |
|-----|----|----|----|----|----|----|------------|
| 57 | 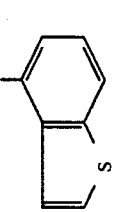 | H | H | CH₃ | trans-ethenylene | $-C\equiv C-\underset{\underset{CH_3}{\|}}{\overset{\overset{CH_3}{\|}}{C}}-CH_3$ | 4 |
| 58 | 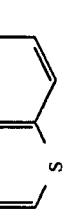 | H | H | CH₃ | trans-ethenylene | $-C\equiv C-\underset{\underset{CH_3}{\|}}{\overset{\overset{CH_3}{\|}}{C}}-CH_3$ | 4 |
| 59 | 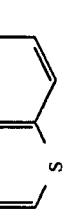 | H | H | CH₃ | trans-ethenylene | $-C\equiv C-\underset{\underset{CH_3}{\|}}{\overset{\overset{CH_3}{\|}}{C}}-CH_3$ | 4 |
| 60 | 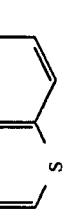 | H | H | CH₃ | trans-ethenylene | $-C\equiv C-\underset{\underset{CH_3}{\|}}{\overset{\overset{CH_3}{\|}}{C}}-CH_3$ | 4 |
| 61 | 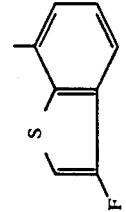 | H | H | CH₃ | trans-ethenylene | $-C\equiv C-\underset{\underset{CH_3}{\|}}{\overset{\overset{CH_3}{\|}}{C}}-CH_3$ | 4 |
| 62 | 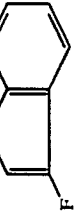 | H | H | CH₃ | trans-ethenylene | $-C\equiv C-\underset{\underset{CH_3}{\|}}{\overset{\overset{CH_3}{\|}}{C}}-CH_3$ | 4 |

TABLE 1-continued

Compounds b $$R^1-\underset{\underset{R^3}{|}}{\overset{\overset{R^2}{|}}{C}}-\underset{}{\overset{\overset{R^4}{|}}{N}}-CH_2-W-R^5 \quad II$$

| No. | R¹ | R² | R³ | R⁴ | W | R⁵ | Known from |
|---|---|---|---|---|---|---|---|
| 63 | 2-NC-benzothiophene | H | H | CH₃ | trans-ethenylene | −C≡C−C(CH₃)₃ | 4 |
| 64 | 2-(HC≡C)-benzothiophene | H | H | CH₃ | trans-ethenylene | −C≡C−C(CH₃)₃ | 4 |
| 65 | 2-(NC−H₂C)-benzothiophene | H | H | CH₃ | trans-ethenylene | −C≡C−C(CH₃)₃ | 4 |
| 66 | 2-Br,3-F-benzothiophene | H | H | CH₃ | trans-ethenylene | −C≡C−C(CH₃)₃ | 4 |
| 67 | 2-(CH₃O−CH₂)-benzothiophene | H | H | CH₃ | trans-ethenylene | −C≡C−C(CH₃)₃ | 4 |
| 68 | α-naphthyl | H | H | CH₃ | trans-ethenylene | −C≡C−C(CH₃)₂−OCH₃ | 5 |

TABLE 1-continued

Compounds b $$R^1-\underset{\underset{R^3}{|}}{\overset{\overset{R^2}{|}}{C}}-\underset{}{\overset{\overset{R^4}{|}}{N}}-CH_2-W-R^5 \quad II$$

| No. | R¹ | R² | R³ | R⁴ | W | R⁵ | Known from |
|---|---|---|---|---|---|---|---|
| 69 | benzothiophene | H | H | CH₃ | trans-ethenylene | $-C{\equiv}C-\underset{CH_3}{\overset{CH_3}{\underset{|}{\overset{|}{C}}}}-OCH_3$ | 5 |
| 70 | chloro-benzothiophene | H | H | CH₃ | trans-ethenylene | $-C{\equiv}C-\underset{CH_3}{\overset{CH_3}{\underset{|}{\overset{|}{C}}}}-OCH_3$ | 5 |
| 71 | α-naphthyl | H | H | CH₃ | trans-ethenylene | $-C{\equiv}C-\underset{CH_3}{\overset{CH_3}{\underset{|}{\overset{|}{C}}}}-OC_2H_5$ | 5 |
| 72 | benzothiophene | H | H | CH₃ | trans-ethenylene | $-C{\equiv}C-\underset{CH_3}{\overset{CH_3}{\underset{|}{\overset{|}{C}}}}-OC_2H_5$ | 5 |
| 73 | α-naphthyl | H | H | CH₃ | trans-ethenylene | $-C{\equiv}C-\underset{CH_3}{\overset{CH_3}{\underset{|}{\overset{|}{C}}}}-CH_2CN$ | 5 |
| 74 | α-naphthyl | H | H | CH₃ | trans-ethenylene | $-C{\equiv}C-\underset{Cl}{\overset{}{\underset{|}{C}}}\overset{Cl}{\underset{}{\diagup\!\!\!\diagdown}}$ | 5 |
| 75 | α-naphthyl | H | H | CH₃ | trans-ethenylene | $-C{\equiv}C-\underset{CH_3}{\overset{CH_3}{\underset{|}{\overset{|}{C}}}}-C_2H_4OCH_3$ | 5 |

TABLE 1-continued

Compounds b $$R^1-\underset{\underset{R_3}{|}}{\overset{\overset{R^2}{|}}{C}}-\underset{\underset{}{|}}{\overset{\overset{R^4}{|}}{N}}-CH_2-W-R^5 \quad II$$

| No. | R$^1$ | R$^2$ | R$^3$ | R$^4$ | W | R$^5$ | Known from |
|---|---|---|---|---|---|---|---|
| 76 | (5,6,7,8-tetrahydronaphthyl) | H | H | CH$_3$ | trans-ethenylene | $-C\equiv C-\underset{\underset{CH_3}{\|}}{\overset{\overset{CH_3}{\|}}{C}}-OCH_3$ | 5 |
| 77 | α-naphthyl | H | H | CH$_3$ | trans-ethenylene | $-C\equiv C-\underset{\underset{CH_3}{\|}}{\overset{\overset{CH_3}{\|}}{C}}-CH_2Cl$ | 5 |
| 78 | α-naphthyl | | =O | CH$_3$ | trans-ethenylene | (phenyl) | 6 |
| 79 | (tetrahydroanthracenyl) | H | H | CH$_3$ | trans-ethenylene | (phenyl) | 7 |
| 80 | (anthracenyl) | H | H | CH$_3$ | trans-ethenylene | (phenyl) | 7 |
| 81 | α-naphthyl | H | H | CH$_3$ | trans-ethenylene | $-C\equiv C-\underset{\underset{C_2H_5}{\|}}{\overset{\overset{C_2H_5}{\|}}{C}}-O_2H_5$ | 8 |
| 82 | α-naphthyl | H | H | CH$_3$ | trans-ethenylene | $-CH=CH-(CH_2)_4-CH_3$ | 8 |
| 83 | α-naphthyl | H | H | CH$_3$ | trans-ethenylene | $-CH=CH-\underset{\underset{CH_3}{\|}}{\overset{\overset{CH_3}{\|}}{C}}-OCH_3$ | 8 |

TABLE 1-continued

Compounds b $$R^1-\underset{\underset{R^3}{|}}{\overset{\overset{R^2}{|}}{C}}-N-CH_2-W-R^5 \quad II$$

| No. | $R^1$ | $R^2$ | $R^3$ | $R^4$ | W | $R^5$ | Known from |
|---|---|---|---|---|---|---|---|
| 84 | α-naphthyl | H | H | $CH_3$ | trans-ethenylene | $-CH=C(CH_3)-C(CH_3)_2-CH_3$ | 8 |
| 85 | α-naphthyl | H | $R^3, R^4, N$ = thiazolidinyl | | trans-ethenylene | $-CH=CH-C(CH_3)_2-OCH_3$ | 9 |
| 86 | α-naphthyl | H | H | $CH_3$ | trans-ethenylene | $-C\equiv C-(CH_2)_3-CH_3$ | 9 |
| 87 | α-naphthyl | H | $R^3, R^4, N$ = pyrrolidinyl | | trans-ethenylene | phenyl | 9 |
| 88 | acenaphthenyl | H | H | $CH_3$ | trans-ethenylene | phenyl | 9 |
| 89 | acenaphthenyl (with $R^1-CR^2R^3$) | | | | trans-ethenylene | $-C\equiv C-C(CH_3)_2-CH_3$ | 9 |

TABLE 1-continued

Compounds b $$R^1-\underset{\underset{R^3}{|}}{\overset{\overset{R^2}{|}}{C}}-\underset{|}{\overset{R^4}{N}}-CH_2-W-R^5 \quad II$$

| No. | R¹ | R² | R³ | R⁴ | W | R⁵ | Known from |
|---|---|---|---|---|---|---|---|
| 90 | (1-methyl-1,2,3,4-tetrahydrophenanthrenyl) | | | CH₃ | trans-ethenylene | phenyl | 9 |
| 91 | 2,3-dimethylphenyl | H | H | CH₃ | trans-ethenylene | phenyl | 10 |
| 92 | 2-chloro-6-methylphenyl | H | H | CH₃ | trans-ethenylene | phenyl | 10 |
| 93 | 4-methoxy-2,3-dimethylphenyl | H | H | CH₃ | trans-ethenylene | phenyl | 10 |
| 94 | 2,3-dimethylphenyl | H | H | R⁴, R³, N (piperidinyl) | trans-ethenylene | phenyl | 10 |

TABLE 1-continued

Compounds b $$R^1-\underset{\underset{R^3}{|}}{\overset{\overset{R^2}{|}}{C}}-\underset{\underset{}{|}}{\overset{\overset{R^4}{|}}{N}}-CH_2-W-R^5$$

| No. | R¹ | R² | R³ | R⁴ | W | R⁵ | Known from |
|-----|-----|-----|-----|-----|-----|-----|-----|
| 95 | 2,5-dimethylphenyl | H | H | CH₃ | trans-ethenylene | phenyl | 10 |
| 96 | 2-methylstyryl | H | H | CH₃ | trans-ethenylene | phenyl | 10 |
| 97 | 2-methylbenzyl | H | H | CH₃ | trans-ethenylene | phenyl | 10 |
| 98 | 2,4-dichlorophenyl | H | H | CH₃ | trans-ethenylene | phenyl | 10 |
| 99 | 2,4-dimethylphenyl | H | H | CH₃ | trans-ethenylene | phenyl | 10 |

TABLE 1-continued

Compounds b $$R^1-\underset{\underset{R_3}{|}}{\overset{\overset{R^2}{|}\ \overset{R^4}{|}}{C}}-N-CH_2-W-R^5 \quad II$$

| No. | R¹ | R² | R³ | R⁴ | W | R⁵ | Known from |
|---|---|---|---|---|---|---|---|
| 100 | 2,4,6-trimethylphenyl (H₃C-C₆H₂(CH₃)₂-) | H | H | CH₃ | trans-ethenylene | phenyl | 10 |
| 101 | 2-styrylphenyl | H | H | CH₃ | trans-ethenylene | phenyl | 10 |
| 102 | α-naphthyl | H | H | CH₃ | CH₂ | $-C\equiv C-\underset{\underset{CH_3}{|}}{\overset{\overset{CH_3}{|}}{C}}-CH_3$ | 11 |
| 103 | α-naphthyl | H | H | CH₃ | CH₂ | $-C\equiv C-\underset{\underset{C_2H_5}{|}}{\overset{\overset{C_2H_5}{|}}{C}}-OH$ | 11 |
| 104 | α-naphthyl | H | H | CH₃ | CH₂ | $-C\equiv C-\underset{\underset{CH-CH_3}{|}}{\overset{\overset{CH_3}{|}}{C}}-C_2H_5$ | 11 |
| 105 | α-naphthyl | H | H | CH₃ | trans-ethenylene | $-C\equiv C-\underset{\underset{CH_3}{|}}{\overset{\overset{CH_3}{|}}{C}}-C_2H_5$ | 12 |
| 106 | α-naphthyl | H | H | CH₃ | CH₂ | $-C\equiv C-\underset{\underset{CH_3}{|}}{\overset{\overset{CH_3}{|}}{C}}-CH_2-phenyl$ | 12 |

TABLE 1-continued
Compounds h
$$R^1-\overset{R^2}{\underset{R^3}{C}}-\overset{R^4}{N}-CH_2-W-R^5 \quad II$$
| No. | $R^1$ | $R^2$ | $R^3$ | $R^4$ | W | $R^5$ | Known from |
|---|---|---|---|---|---|---|---|
| 107 | α-naphthyl | H | H | CH$_3$ | CH$_2$ |  | 13 |
| 108 | α-naphthyl | H | H | CH$_3$ | CH$_2$ | 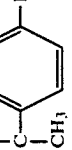 | 13 |
| 109 | α-naphthyl | H | H | CH$_3$ | CH$_2$ | 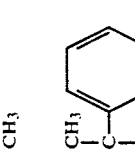 | 13 |
| 110 | α-naphthyl | H | H | CH$_3$ | —CH$_2$—CH$_2$— | 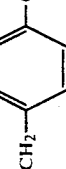 | 13 |
| 111 | α-naphthyl | H | H | CH$_3$ | 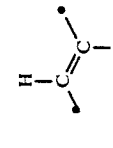 (trans-ethenylene) |  | 14 |
| 112 | α-naphthyl | H | H | CH$_3$ | trans-ethenylene | 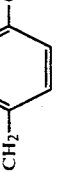 | 14 |
| 113 | α-naphthyl | H | H | CH$_3$ | trans-ethenylene | 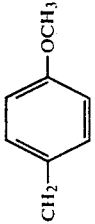 | 14 |

TABLE 1-continued

Compounds b $$R^1-\underset{\underset{R_3}{|}}{\overset{\overset{R^2}{|}}{C}}-\overset{\overset{R^4}{|}}{N}-CH_2-W-R^5 \quad \text{II}$$

| No. | R¹ | R² | R³ | R⁴ | W | R⁵ | Known from |
|-----|-----|-----|-----|-----|-----|-----|-----|
| 114 | α-naphthyl | H | H | CH₃ | trans-ethenylene |  | 14 |
| 115 | α-naphthyl | H | H | CH₃ | trans-ethenylene |  | 14 |
| 116 | α-naphthyl | H | H | CH₃ | trans-ethenylene |  | 14 |
| 117 | α-naphthyl | H | H | CH₃ | trans-ethenylene |  | 14 |
| 118 | α-naphthyl | H | H | CH₃ | 1-fluoro-trans-ethenylene |  | 15 |
| 119 | α-naphthyl | H | H | CH₃ | 2-fluoro-trans-ethenylene |  | 15 |
| 120 | α-naphthyl | H | H | CH₃ | 1-fluoro-trans-ethenylene |  | 15 |

TABLE 1-continued

Compounds b $$R^1-\underset{\underset{R^3}{|}}{\overset{\overset{R^2}{|}}{C}}-\overset{\overset{R^4}{|}}{N}-CH_2-W-R^5 \quad II$$

| No. | $R^1$ | $R^2$ | $R^3$ | $R^4$ | W | $R^5$ | Known from |
|---|---|---|---|---|---|---|---|
| 121 | α-naphthyl | H | H | CH₃ | 2-fluoro-trans-ethenylene | —C≡C—C(CH₃)₃ | 15 |
| 122 | benzothiophenyl | H | H | CH₃ | 1-fluoro-trans-ethenylene | —C≡C—C(CH₃)₂CN | 15 |
| 123 | 5,8-difluoronaphthyl | H | H | CH₃ | — | 4-(C(CH₃)₃)phenyl | 16 |
| 124 | α-naphthyl | H | H | CH₃ | — | 4-(C(CH₃)₃)phenyl | 16 |
| 125 | α-naphthyl | H | H | CH₃ | — | 4-(CH₂-(4-OCH₃-phenyl))phenyl | 16 |
| 126 | α-naphthyl | H | H | CH₃ | — | 4-(C≡C—C(CH₃)₃)phenyl | 16 |
| 127 | α-naphthyl | H | H | CH₃ | — | 4-phenyl-phenyl | 16 |

TABLE 1-continued

Compounds h $$R^1 - \underset{\underset{R^3}{|}}{\overset{\overset{R^2}{|}}{C}} - \underset{\underset{R^3}{|}}{\overset{R^4}{N}} - CH_2 - W - R^5 \qquad II$$

| No. | $R^1$ | $R^2$ | $R^3$ | $R^4$ | W | $R^5$ | Known from |
|---|---|---|---|---|---|---|---|
| 128 | α-naphthyl | H | H | $CH_3$ | — | 3,5-dimethylphenyl | 16 |
| 129 | benzo[d][1,3]dioxol-4-yl | H | H | $CH_3$ | — | 3,5-dimethylphenyl | 16 |
| 130 | α-naphthyl | H | \[piperidinyl: $R^3, R^4, N$\] | | — | 4-(2-phenylpropan-2-yl)phenyl | 16 |
| 131 | α-naphthyl | H | H | $CH_3$ | — | 1,1-bis(4-methylphenyl)propyl-type | 16 |
| 132 | acenaphthylenyl ($R^1-C(R^3)-R^2$) | | | | — | 4-(2-methylpropan-2-yl)phenyl | 16 |

TABLE 1-continued
Compounds b
$$R^1-\underset{\underset{R_3}{|}}{\overset{\overset{R^2}{|}}{C}}-N-CH_2-W-R^5$$
II
| No. | $R^1$ | $R^2$ | $R^3$ | $R^4$ | W | $R^5$ | Known from |
|---|---|---|---|---|---|---|---|
| 133 | α-naphthyl | H | H | $CH_3$ | — | 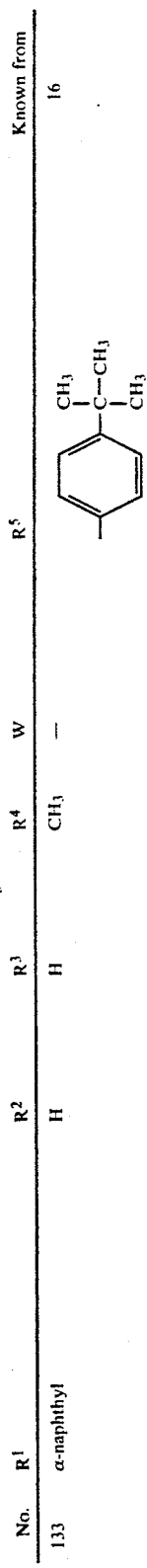 | 16 |
| 134 | α-naphthyl | H | H | cyclo-propyl | — | 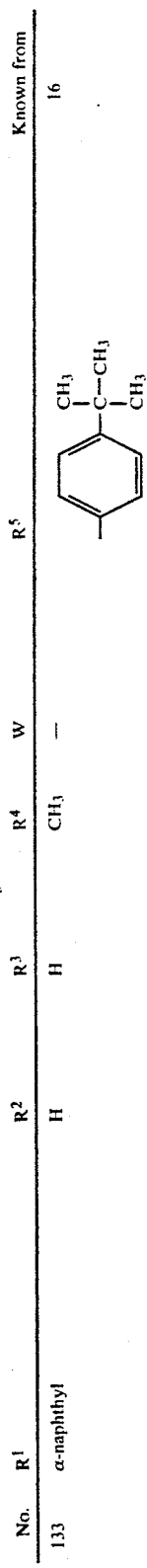 | 16 |
| 135 | α-naphthyl | H | H | $CH_3$ | — | 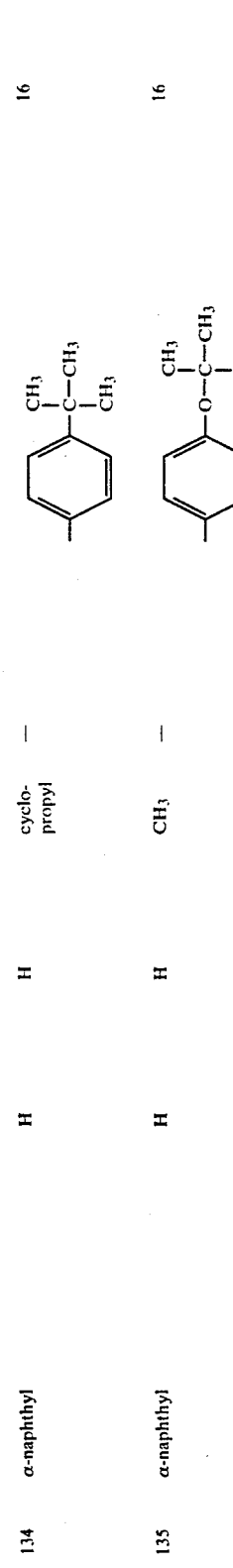 | 16 |
| 136 | α-naphthyl | H | H | $-CH_2-CH_2F$ | — | 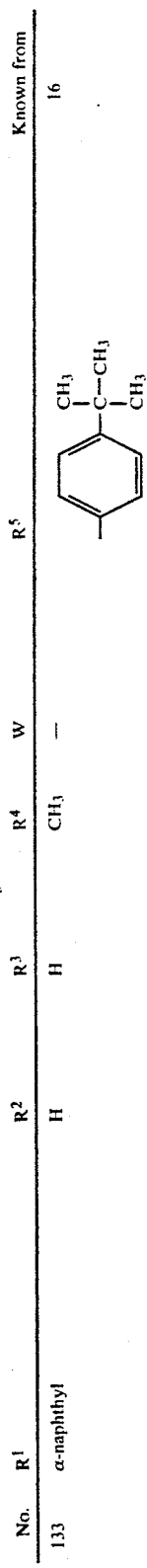 | 16 |
| 137 | α-naphthyl | H | H | $CH_3$ | — | 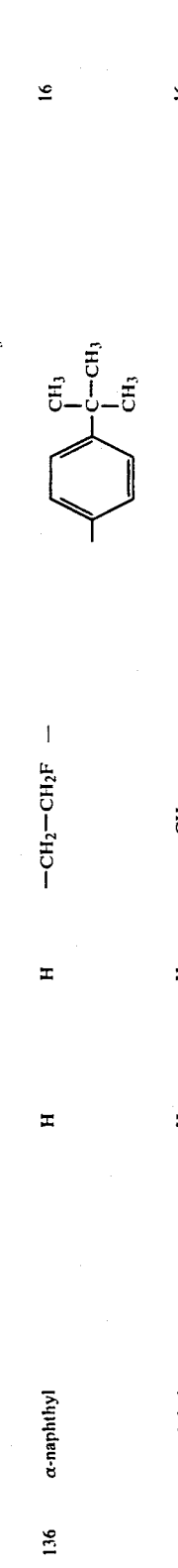 | 16 |
| 138 | α-naphthyl | H | H | $CH_3$ | — | 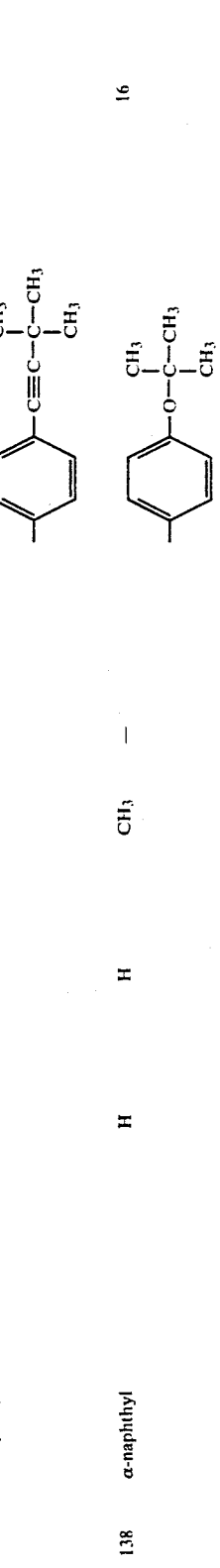 | 16 |
| 139 | α-naphthyl | H | H | $CH_3$ | — | 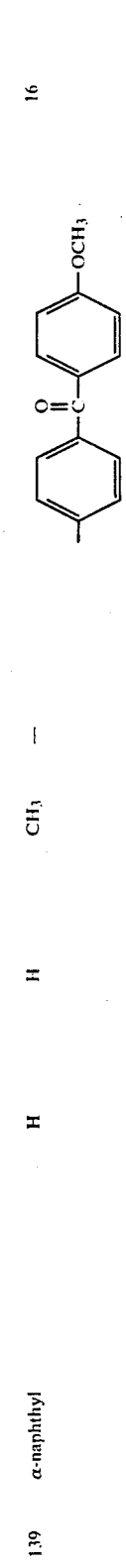 | 16 |

TABLE 1-continued

Compounds b $$R^1-\overset{R^2}{\underset{R_3}{C}}-\overset{R^4}{\underset{}{N}}-CH_2-W-R^5 \quad II$$

| No. | R¹ | R² | R³ | R⁴ | W | R⁵ | Known from |
|-----|----|----|----|----|---|----|------------|
| 140 | α-naphthyl | H | H | CH₃ | — | C(CH₃)(p-tolyl)(p-tolyl) with extra p-CH₃-phenyl | 16 |
| 141 | α-naphthyl | H | H | CH₃ | — | C(C₂H₅)(C₂H₅)(C₂H₅)-(p-tolyl) | 16 |
| 142 | [2-chlorobenzothiophene] | H | H | CH₃ | — | C(CH₃)(CH₃)(CH(CH₃)₂)-(p-tolyl) | 16 |
| 143 | α-naphthyl | H | H | C₂H₅ | — | C(CH₃)(CH₃)(CH₃)-(p-tolyl) | 16 |
| 144 | α-naphthyl | H | H | CH₃ | — | C(CH₃)(C₂H₅)(CH₃)-(p-tolyl) | 16 |
| 145 | α-naphthyl | H | H | CH₃ | — | C(CH₃)(CH(CH₃)₂)(CH₃)-(m-tolyl) | 16 |
| 146 | α-naphthyl | H | H | CH₃ | — | p-tolyl-O-(CH₂)₄-CH₃ | 16 |

TABLE 1-continued

Compounds b $$R^1-\underset{\underset{R^3}{|}}{\overset{\overset{R^2}{|}}{C}}-\underset{}{\overset{\overset{R^4}{|}}{N}}-CH_2-W-R^5 \quad II$$

| No. | R¹ | R² | R³ | R⁴ | W | R⁵ | Known from |
|---|---|---|---|---|---|---|---|
| 147 | 2,3-dimethylphenyl | H | H | CH₃ | — | 4-(2-methylpropan-2-yl)phenyl | 16 |
| 148 | 2-methoxy-3-methyl-6-(2-methylpropan-2-yl)phenyl | H | H | CH₃ | — | 4-(2-methylpropan-2-yl)phenyl | 16 |
| 149 | 2,3-dichlorophenyl | H | H | CH₃ | — | 4-(2-methyl-1-phenylpropan-2-yl)phenyl | 16 |
| 150 | 2,3-dichlorophenyl | H | H | CH₃ | — | 4-(2-methylpropan-2-yl)phenyl | 16 |
| 151 | α-naphthyl | H | H | CH₃ | — | 4-(4-methylbenzyl)phenyl | 16 |
| 152 | α-naphthyl | H | H | CH₃ | — | 5-methyl-2-(2-methylpropan-2-yl)pyridyl | 16 |
| 153 | α-naphthyl | H | H | CH₃ | = | β-naphthyl | 17 |
| 154 | α-naphthyl | H | H | CH₃ | = | α-naphthyl | 17 |

TABLE 1-continued

Compounds b $$R^1-\underset{\underset{R^3}{|}}{\overset{\overset{R^2}{|}}{C}}-\underset{\underset{}{|}}{\overset{\overset{R^4}{|}}{N}}-CH_2-W-R^5 \quad II$$

| No. | R¹ | R² | R³ | R⁴ | W | R⁵ | Known from |
|---|---|---|---|---|---|---|---|
| 155 | 2-methylnaphthyl | H | H | CH₃ | — | β-naphthyl | 17 |
| 156 | 4-chloro-1-methylnaphthyl | H | H | CH₃ | — | 4-(2-methyl-2-propyl)phenyl (tolyl-C(CH₃)₃) | 18 |
| 157 | 4-bromo-1-methylnaphthyl | H | H | CH₃ | — | 4-(2-methyl-2-propyl)phenyl | 18 |
| 158 | 2-methoxy-1-methylnaphthyl | H | H | CH₃ | — | 4-(2-methyl-2-propyl)phenyl | 18 |
| 159 | 4-chloro-1-methylnaphthyl | H | H | CH₃ | — | α-naphthyl | 18 |

TABLE 1-continued

Compounds b $$R^1-\underset{\underset{R^3}{|}}{\overset{\overset{R^2}{|}}{C}}-\underset{}{\overset{R^4}{|}}{N}-CH_2-W-R^5 \quad II$$

| No. | R¹ | R² | R³ | R⁴ | W | R⁵ | Known from |
|---|---|---|---|---|---|---|---|
| 160 | 1,4-dimethylnaphthyl (structure) | H | H | CH₃ | — | β-naphthyl | 18 |
| 161 | α-naphthyl | H | H | C₂H₅ | — | α-naphthyl | 18 |
| 162 | α-naphthyl | H | H | C₂H₅ | — | β-naphthyl | 18 |
| 163 | α-naphthyl | H | H | n-C₃H₇ | — | β-naphthyl | 18 |
| 164 | α-naphthyl | H | H | n-C₄H₉ | — | β-naphthyl | 17 |
| 165 | α-naphthyl | H | H | n-C₄H₉ | — | β-naphthyl | 17 |
| 166 | α-naphthyl | H | H | isopropyl | — | p-tert-butylphenyl | 19 |
| 167 | α-naphthyl | H | H | allyl | — | p-tert-butylphenyl | 19 |

TABLE 1-continued

Compounds b $$R^1-\overset{R^2}{\underset{R_3}{\overset{|}{C}}}-\overset{R^4}{\underset{|}{N}}-CH_2-W-R^5 \quad II$$

| No. | R¹ | R² | R³ | R⁴ | W | R⁵ | Known from |
|---|---|---|---|---|---|---|---|
| 168 | 9-anthracenyl | H | H | CH₃ | — | 4-(2-methyl-2-propyl)phenyl (C(CH₃)₃) | 19 |

Footnotes:
1) DE 2716943
2) DE 2809211
3) EP 0024587
4) DE 3302814
5) DE 3316093
6) DE 3405329
7) DE 3405330
8) DE 3405832
9) DE 3405444
10) DE 3405334
11) DE 3442529
12) DE 3528736
13) EP 0191269
14) EP 0254677
15) DE 3631297
16) DE 3702039
17) J 6 0172-919-A
18) EP 0164697
19) EP 0221781

Generally speaking, the novel compounds are extremely effective on a broad spectrum of phytopathogenic fungi, in particular those from the Ascomycetes and Basidiomycetes classes. Some of them have a systemic action and can be used as foliar and soil fungicides.

The fungicidal mixtures are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel mixtures are particularly useful for controlling the following plant diseases:

*Erysiphe graminis* in cereals,
*Erysiphe cichoracearum* and *Sphaerotheca fuliginea* in cucurbits,
*Podosphaera leucotricha* in apples,
*Uncinula necator* in vines,
Puccinia species in cereals,
Rhizoctonia species in cotton and lawns,
Ustilago species in cereals and sugar cane,
*Venturia inaequalis* (scab) in apples,
Helminthosporium species in cereals,
*Septoria nodorum* in wheat,
*Botrytis cinerea* (gray mold) in strawberries and grapes,
*Cercospora arachidicola* in groundnuts,
*Pseudocercosporella herpotrichoides* in wheat and barley,
*Pyricularia oryzae* in rice,
*Phytophthora infestans* in potatoes and tomatoes,
Fusarium and Verticillium species in various plants,
*Plasmopara viticola* in grapes,
Alternaria species in fruit and vegetables.

The mixtures are applied by spraying or dusting the plants with the active ingredients, or treating the seeds of the plants with the active ingredients. They may be applied before or after infection of the plants or seeds by the fungi.

The mixtures can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin, sulfite waste liquors and methylcellulose.

The fungicidal agents generally contain from 0.1 to 95, and preferably from 0.5 to 90, wt % of active ingredient. The application rates are from 0.02 to 3 kg or more of mixture per hectare, depending on the type of effect desired. The novel mixtures may also be used for protecting materials, for example against Paecilomyces variotii.

The fungicidal agents and the ready-to-use formulations prepared from them, such as solutions, emulsions, suspensions, powders, dusts, pastes and granules, are applied in conventional manner, for example by spraying, atomizing, dusting, scattering, dressing or watering.

Examples of formulations are given below.

I. 90 parts by weight of mixture 1 is mixed with 10 parts by weight of N-methyl-α-pyrrolidone. A mixture is obtained which is suitable for application in the form of very fine drops.

II. 20 parts by weight of mixture 1 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of mixture 1 is dissolved in a mixture consisting of 40 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of mixture 1 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of mixture 1 is well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of mixture 1 is intimately mixed with 97 parts by weight of particulate kaolin. A dust is obtained containing 3% by weight of the active ingredient.

VII. 30 parts by weight of mixture 1 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of mixture 1 is intimately mixed with 10 parts by weight of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts by weight of mixture 1 is intimately mixed with 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil. A stable oily dispersion is obtained.

In these application forms, the agents according to the invention may also be present together with other active ingredients, for example herbicides, insecticides, growth regulators, and fungicides, and may furthermore be mixed and applied together with fertilizers. Admixture with other fungicides frequently results in an increase in the fungicidal spectrum.

USE EXAMPLE 1

Action on *Pyrenophora teres*

Barley seedlings of the Igri variety were sprayed to runoff at the 2-leaf stage with aqueous suspensions containing (dry basis) 80% of active ingredient and 20% of emulsifier. After 24 hours the plants were inoculated with a spore suspension of the fungus *Pyrenophora teres* and placed for 48 hours in a high-humidity climatic cabinet at 18° C. The plants were then cultivated for a further 5 days in the greenhouse at 20°–22° C. and a relative humidity of 70%. The spread of the symptoms was then assessed.

The action was evaluated according to the following formula (Abbott):

$$\text{Degree of action} = 1 - \frac{\text{Attack in \% (treated)}}{\text{Attack in \% (untreated)}} \times 100$$

| Active ingredient no. | Appl. rate ... ppm | Degree of action ... % |
|---|---|---|
| fenpropimorph | 125 | 50 |
| 1 | 125 | 0 |
| fenpropimorph + 1 | 125 125 | 75 |

USE EXAMPLE 2

Action on Mildew in Grapes

Leaves of potted vines of the Müller-Thurgau variety were sprayed with aqueous suspensions containing (dry basis) 80% of active ingredient and 20% of emulsifier. To assess the duration of action, the plants were set up, after the sprayed-on layer had dried, for 8 days in the greenhouse. Then the leaves were infected with a zoospore suspension of Plasmopara viticola. The plants were first placed for 48 hours in a water vapor-saturated chamber at 24° C. and then in a greenhouse for 5 days at from 20° to 30° C. To accelerate and intensify the sporangiophore discharge, the plants were then again placed in the moist chamber for 16 hours. The extent of fungus attack was then assessed on the undersides of the leaves. The degree of action was assessed in accordance with the Abbott formula.

| Active ingredient no. | Appl. rate ... ppm | Degree of action ... % |
|---|---|---|
| fenpropimorph | 500 | 0 |
| 1 | 500 | 25 |
| fenpropimorph + Active ingredient 1 | 500 500 | 37.5 |

USE EXAMPLE 3

One liter of an aqueous solution containing 3 g/liter of malt extract, 3 g/liter of yeast extract, 5 g/liter of bacto-peptone and 10 g of glucose/liter is inoculated with the fungus causing corn smut (Ustilago maydis) and then shaken for 18 hours at 23° C. To test the fungicidal effectiveness of the individual active ingredients they are dissolved in ethanol and added to the aqueous solution before inoculation with the fungus. After 18 hours the amount of fungus culture in the aqueous solution (dry weight) is determined spectroscopically by measurement at 540 nm, followed by comparison with a calibration curve. The growth inhibition in % is set in relation to the value of the liquid culture to which only ethanol (no active ingredient) has been added. Growth inhibition in the liquid without active ingredient is set at 0%. Concentrations of the active ingredients are given in moles/liter. Growth inhibition is given in %.

| Active ingredient | Concentration | Growth found | inhibition calculated (sum of individual actions) | Mixture ratio act. ingr.: fenpropimorph |
|---|---|---|---|---|
| 1 | $5 \times 10^{-7}$ | 0 | | |
| fenpropimorph | $5 \times 10^{-9}$ | 0 | | |
| 1 + fenpropimorph | $5 \times 10^{-7}$ + $5 \times 10^{-9}$ | 16 | 0 | 100:1 |
| 1 | $1 \times 10^{-6}$ | 0 | | |
| fenpropimorph | $1 \times 10^{-8}$ | 9 | | |
| 1 + fenpropimorph | $1 \times 10^{-6}$ + $1 \times 10^{-8}$ | 42 | 9 | 100:1 |
| 1 | $5 \times 10^{-6}$ | 0 | | |
| fenpropimorph | $5 \times 10^{-8}$ | 34 | | |
| 1 + fenpropimorph | $5 \times 10^{-6}$ + $5 \times 10^{-8}$ | 78 | 34 | 100:1 |

USE EXAMPLE 4

Action on Bean Rust

Leaves of bush beans of the "Fori" variety were sprayed at the true-leaf stage with aqueous spray liquors containing (dry basis) 90% of active ingredient and 10% of emulsifier. After the sprayed-on layer had dried, the plants were set up for 24 hours in a greenhouse at 18° C. After inoculation with an aqueous spore suspension of bean rust (Uromyces appendiculatus) the plants were kept for 24 hours in a high-humidity climatic cabinet at 16° C., and then set up in the greenhouse at 20° to 22° C. The spread of pustules on the true leaves was assessed 13 days after inoculation.

The degree of action was assessed in accordance with the following formula (Abbott):

$$\text{Degree of action} = 1 - \frac{\text{Attack in \% (treated)}}{\text{Attack in \% (untreated)}} \times 100$$

| Active ingredient | Appl. rate ... ppm | Degree of action ... % |
|---|---|---|
| fenpropimorph | 5 | 17 |
| | 10 | 44 |
| naftifin | 1 | 0 |
| (act. ingr. 1 from Table 1) | 20 | 6 |
| | 50 | 6 |
| | 100 | 22 |
| fenpropimorph + naftifin | 5 + 1 | 44 |
| | 5 + 20 | 44 |
| | 5 + 50 | 67 |
| | 5 + 100 | 69 |
| | 10 + 1 | 50 |
| | 10 + 20 | 67 |
| | 10 + 50 | 69 |
| | 10 + 100 | 86 |

We claim:
1. A fungicidal mixture of
a) a compound of the formula I

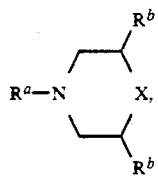

where
$R^a$ = 3-(p-tert-butyl-(phenyl)-2-methylpropyl,
$R^b$ = CH$_3$ (cis or trans) and
X = O,
and b) a compound of the formula II

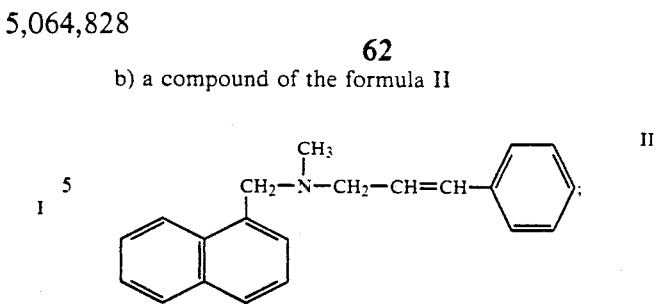

wherein the synergistic ratio of a:b being 1:100–10:1.

2. The fungicidal mixture as set forth in claim 1, containing the two active ingredients a:b in a weight ratio of from 1:5 to 1:1.

3. A process for combating fungi, wherein the fungi, or plants, seeds, or the soil attacked by said fungi are treated with a fungicidally effective amount of a mixture as set forth in claim 1.

* * * * *